United States Patent [19]

Storni

[11] Patent Number: 4,582,841
[45] Date of Patent: Apr. 15, 1986

[54] SUBSTITUTED THIAZOLIDINYL ESTERS OF MINERAL ACIDS

[75] Inventor: Angelo Storni, Rheinfelden, Switzerland

[73] Assignee: Ciba-Geigy Corporation, Ardsley, N.Y.

[21] Appl. No.: 630,136

[22] Filed: Jul. 12, 1984

Related U.S. Application Data

[63] Continuation-in-part of Ser. No. 434,304, Oct. 14, 1982, Pat. No. 4,489,069.

[30] Foreign Application Priority Data

Jul. 19, 1983 [CH] Switzerland .......... 3946/83

[51] Int. Cl.⁴ .......... C07D 417/12; A61K 31/425
[52] U.S. Cl. .......... 514/369; 548/117
[58] Field of Search .......... 424/202, 270; 548/117, 548/183; 514/369

[56] References Cited

U.S. PATENT DOCUMENTS 4,489,069 12/1984 Storni .......... 424/202

Primary Examiner—Robert Gerstl
Attorney, Agent, or Firm—Michael W. Glynn

[57] ABSTRACT

Compounds of the formula

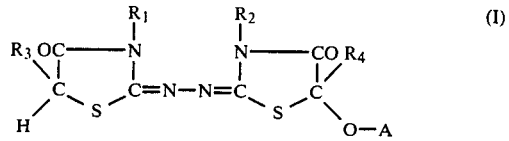

in which one of the symbols $R_1$ and $R_2$ represents an alkyl radical that has 3 or 4 carbon atoms and is unsaturated in the 2,3-position, and the other represents such a radical or lower alkyl, $R_3$ and $R_4$ each represents, independently of the other, hydrogen or methyl, and A represents a radical of the formula

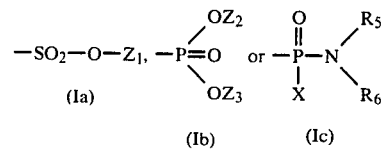

in which $Z_1$, or each of $Z_2$ and $Z_3$ independently of the other, represents hydrogen or lower alkyl, or $Z_2$ and $Z_3$ together represent lower alkylene, each of $R_5$ and $R_6$, independently of the other, represents hydrogen, lower alkyl, halogenated lower alkyl, or lower alkenyl or $R_5$ and $R_6$ together represent lower alkylene that is optionally interrupted by oxygen, sulphur or by optionally substituted nitrogen, and X represents $OR_7$ or $NR_8R_9$ in which $R_7$ represents hydrogen or lower alkyl and each of $R_8$ and $R_9$, independently of the other, represents hydrogen, lower alkyl, halogenated lower alkyl, or lower alkenyl or $R_8$ and $R_9$ together represent lower alkylene that is optionally interrupted by oxygen, sulphur or by optionally substituted nitrogen, or $R_6$ together with $R_7$ or $R_8$ represents a lower alkylene group Alk, and salts of such compounds in which $Z_1$, or $Z_3$ and optionally also $Z_2$, or $R_7$ represent(s) hydrogen, exhibit tumor-inhibiting activities.

11 Claims, No Drawings

SUBSTITUTED THIAZOLIDINYL ESTERS OF MINERAL ACIDS

CROSS REFERENCE

This is a continuation-in-part of my copending application Ser. No. 434,304, filed Oct. 14, 1982 U.S. Pat. No. 4,489,069.

The invention relates to novel substituted thiazolidinyl esters of mineral acids and to salts of such compounds having valuable pharmacological properties, to processes for the manufacture of these novel substances, to pharmaceutical preparations that contain these substances and to the use of these substances and preparations containing them.

The compounds according to the invention correspond general formula

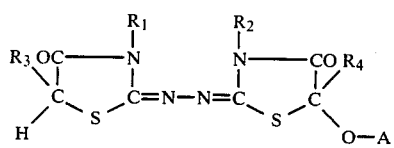
(I)

in which one of the symbols $R_1$ and $R_2$ represents an alkyl radical that has 3 or 4 carbon atoms and is unsaturated in the 2,3-position, and the other represents such a radical or lower alkyl, $R_3$ and $R_4$ each represents, independently of the other, hydrogen or methyl, and A represents a radical of the formula

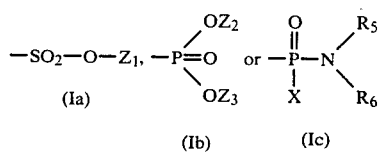

in which $Z_1$, or each of $Z_2$ and $Z_3$, independently of the other, represents hydrogen or lower alkyl, or $Z_2$ and $Z_3$ together represent lower alkylene, each of $R_5$ and $R_6$, independently of the other, represents hydrogen, lower alkyl, halogenated lower alkyl, or lower alkenyl or $R_5$ and $R_6$ together represent lower alkylene that is optionally interrupted by oxygen, sulphur or by optionally substituted nitrogen, and X represents $OR_7$ or $NR_8R_9$ in which $R_7$ represents hydrogen or lower alkyl and each of $R_8$ and $R_9$, independently of the other, represents hydrogen, lower alkyl, halogenated lower alkyl, or lower alkenyl or $R_8$ and $R_9$ together represent lower alkylene that is optionally interrupted by oxygen, sulphur or by optionally substituted nitrogen, or $R_6$ together with $R_7$ or $R_8$ represents a lower alkylene group Alk. The invention relates also to salts of compounds of the general formula I in which $Z_1$, or $Z_3$ and optionally also $Z_2$, or $R_7$, represent(s) hydrogen, with bases, especially to the pharmaceutically acceptable salts with bases.

In compounds of the general formula I, an alkyl radical $R_1$ and/or $R_2$ that is unsaturated in the 2,3-position contains a double or triple bond and represents, for example, corresponding lower alkenyl, such as allyl or 1- or 2-methylallyl, or corresponding lower alkynyl, for example 2-propynyl.

Lower alkyl contains up to 7, preferably up to 4, carbon atoms and is, for example, pentyl, isopentyl, neopentyl, hexyl or heptyl, preferably propyl, 2-propyl, butyl or isobutyl, but above all ethyl and especially methyl.

Halogenated lower alkyl contains up to 7, preferably up to 4, carbon atoms and is halogenated, such as, for example, brominated or, preferably, chlorinated, one or more times, especially once or twice, in the 1-, 2- or 3-position or, alternatively, in a higher position, and is, for example, chloropropyl, such as 1-, 2- or 3-chloropropyl, or especially chloroethyl, such as 1- or 2-chloroethyl, dichloroethyl, such as 1,1-, 1,2- or 2,2-dichloroethyl, or chloromethyl.

A lower alkenyl radical contains up to 7, preferably from 3 to 5, carbon atoms and has the double bond especially in a position higher than the 1-position and is, for example, allyl, 1- or 2-methylallyl, but-2-en-1-yl, pent-2- or pent-3-en-1-yl or, alternatively, 1- or 2-methylvinyl.

Lower alkylene that is optionally interrupted by oxygen, sulphur or by optionally substituted nitrogen, such as nitrogen containing lower alkyl, for example methyl, and that can be formed by $R_5$ and $R_6$ together or by $R_8$ and $R_9$ together contains preferably 4 or 5 chain atoms and is, for example, 1,4-butylene, 1,5-pentylene, 3-oxa-1,5-pentylene, 3-thia-1,5-pentylene, 3-aza-1,5-pentylene or 3-methyl-3-aza-1,5-pentylene.

A radical $R_6$ which, together with $R_7$, forms a lower alkylene group Alk separates the two hetero atoms preferably by from 2 to 4 carbon atoms and represents, for example, a 1,4-butylene, a 1,3-propylene or, especially, a 1,2-ethylene group, so that $R_6$ and $R_7$ represent, including the atom grouping N-P-O, for example, substituted perhydro-1,3,2-oxaza-phosphepine or -phosphorine or, especially, 1,3,2-oxazaphospholidine.

A radical $R_6$ together with $R_8$ can represent a lower alkylene radical Alk which separates the two nitrogen atoms preferably by from 2 to 4 carbon atoms, for example a 1,4-butylene, a 1,3-propylene or, especially, a 1,2-ethylene group, so that $R_6$ and $R_8$ represent, including the atom grouping N-P-N, for example, substituted perhydro-1,3,2-diaza-phosphepine or -phosphorine or, especially, 1,3,2-diazaphospholidine.

Lower alkylene formed by $Z_2$ and $Z_3$ together has from 2 to 5 carbon atoms with 3 or, preferably, 2 chain members and is, for example, propylene, 1,2-dimethylethylene, trimethylene, 2-methyltrimethylene, 1,3- or 2,2-dimethyltrimethylene or, especially, ethylene.

Salts with bases of compounds of the general formula I that are capable of salt formation are, for example, metal salts, such as alkali metal salts, for example sodium or potassium salts, or alkaline earth metal salts, such as magnesium or calcium salts, and also ammonium salts and salts with primary, secondary or tertiary monoacidic or polyacidic organic bases, such as, for example, ethylamine, 2-aminoethanol, diethylamine, iminodiethanol, triethylamine, 2-(diethylamino)-ethanol, nitrilotriethanol or pyridine, or 1,2-ethanediamine. The corresponding pharmaceutically acceptable, non-toxic salts are preferred.

Compounds of the general formula I having a radical A of the partial formula Ib can, according to the definitions of $Z_2$ and $Z_3$, be in the form of either neutral phosphoric acid esters or acidic, that is to say monobasic (with $Z_2$ as lower alkyl and $Z_3$ as hydrogen or dibasic (with $Z_2$ and $Z_3$ as hydrogen), phosphoric acid esters.

The compounds of the formula I can be in the form of isomeric mixtures, for example mixtures of racemates (diastereoisomeric mixture.) or racemates, or in the form of pure isomers, for example pure racemates or optical antipodes.

The novel compounds of the general formula I and the salts of such compounds exhibit valuable pharmacological properties, especially tumour-inhibiting activity. This can be demonstrated in tests on animals, for example by the oral or parenteral, such as intraperitoneal or subcutaneous, administration of doses of between 10 and 250 mg/kg in Ehrlich carcinoma in mice (transplant: $1 \times 10^6$ cells (Ascites) i.p. to female mice NMRI), in Walker carcinosarooma 256 in rats (transplant: 0.5 ml of a suspension of solid tumours in Hanks solution s.c. or i.m. to male rats (Wistar)), in transplantable mammary adenocarcinoma R 3230 AC in rats (transplant: 0.5 ml of a suspension of solid tumours in Hanks solution s.c. or i.m. to female rats (Fischer)), on subcutaneously transplanted B16-melanoma in mice (transplant: 0.2 ml of a tumour suspension in Hanks solution s.c.) and especially in mammary carcinoma in rats induced by 7,12-dimethylbenz[α]anthracene (DMBA) (induced by the p.o. administration of 15 mg of DMBA in 1 ml of sesame oil to 50 day old female rats (Sprague Dawley), it being possible to detect multiple tumours after 6 to 8 weeks.).

Thus, for example, in Ehrlich carcinoma, after intraperitoneal administration 4 times (4 hours after, and then 1, 2 and 3 days after transplantation: 10 animals per dose; the quantity of Ascites in ml is determined 10 days after transplantation); in Walker carcinosarcoma 256, after oral or intraperitoneal administration four times (1, 2, 3 and 4 days after transplantation; 8 to 10 animals per dose; the tumour weight in grams is determined 10 days after transplantation), and in mammary adenocarcinoma R 3230 AC, after oral or intraperitoneal administration 10 times (5 times per week for two weeks commencing 4 hours after transplantation; 10 to 15 animals per dose; the tumour weight in grams is determined 20 days after transplantation), it is possible to detect the following inhibition of tumour growth in comparison with untreated control animals:

| Compound (Example) | Ehrlich Ascites carcinoma dose (mg/kg) | Inhibition of tumour growth (in %) | Walker carcinosarcoma 256 dose (mg/kg) | Inhibition of tumour growth (in %) | mammary adenocarcinoma R 3230 Ac dose (mg/kg) | Inhibition of tumour growth (in %) |
| --- | --- | --- | --- | --- | --- | --- |
| 1 | 4 × 50 i.p. | 94 | 4 × 50 i.p. | 84 | 10 × 50 i.p. | 62 |
|   |             |    | 4 × 250 p.o. | 53 | 10 × 250 p.o. | 43 |
| 5 | 4 × 50 i.p. | 42 | 4 × 50 p.o. | 72 | — | — |
| 6 | 4 × 100 i.p. | 70 | 4 × 100 i.p. | 53 | — | — |
| 7 | 4 × 100 i.p. | 51 | 4 × 50 i.p. | 31 | — | — |
|   |             |    | 4 × 250 p.o. | 32 | — | — |
| 10 | 4 × 50 i.p. | 21 | — | — | — | — |
| 11 | 4 × 50 i.p. | 49 | — | — | — | — |

(Method of administration: i.p.: intraperitoneal, and p.o.: oral)

In the case of DMBA-induced mammary carcinoma, the following inhibition of tumour growth and of the re-formation of tumours can be detected after treatment for 5 weeks (25 individual doses) and 6 weeks (30 individual doses); (the figures given shown the average size of all tumours in all the test animals):

| Compound (Example) | dose mg/kg | average tumour size (treated/ untreated test animals) (a) | tumour reduction (in percent) |
| --- | --- | --- | --- |
| 1 | 30 × 10 s.c. | 1.13/24.73 | 95 |
|   | 30 × 25 p.o. | 2.50/20.63 | 88 |
| 5 | 25 × 25 i.p. | 6.31/15.97 | 61 |
| 6 | 25 × 100 p.o. | 0.96/19.03 | 95 |
| 6 | 25 × 100 p.o. | 2.13/21.55 | 90 |
| 7 | 30 × 10 s.c. | 2.27/24.82 | 91 |
|   | 30 × 25 p.o. | 6.38/21.04 | 70 |
| 10 | 30 × 10 s.c. | 8.77/22.27 | 61 |
|   | 30 × 25 p.o. | 6.07/22.27 | 72 |
| 11 | 30 × 10 s.c. | 9.03/22.27 | 59 |
|   | 30 × 25 p.o. | 5.65/22.27 | 75 |

(Method of administration: s.c.: subcutaneous; p.o.: oral; i.p.: intraperitoneal; (a): the figures given show the average size of all tumours in all the test animals).

The growth of subcutaneously transplanted B16-melanoma in mice is very strongly inhibited by 10 oral administrations (five times per week for 2 weeks) of 250 mg/kg or 125 mg/kg of the compounds according to the invention, for example, in the case of phosphoric acid dimethylamide methyl ester-[3-methyl-2-[[5-methyl-3-(2-methylallyl)-4-oxo-2-thiazolidinylidene]-hydrazono]-4-oxo-5-thiazolidinyl]-ester, by 53% or 42%, respectively.

In comparison with the strong tumour-inhibiting activity, the toxicity and side-effects of the compounds according to the invention are low to moderate (maximum single dose tolerated:- intraperitoneal administration: between 500 and 1250 mg/kg; and oral administration: more than 2500 mg/kg), so that they can be used as such or, especially, in the form of pharmaceutical preparations for the treatment of neoplastic diseases in warm-blooded animals, especially humans, by enteral, especially oral, or parenteral administration of therepeutically effective doses, and especially for the treatment of mammary carcinoma and carcinoma of the prostate.

The invention relates especially to those compounds of the general formula I in which one of the radicals $R_1$ and $R_2$ represents allyl or 2-methallyl, and the other also represents one of these groups or, preferably, methyl, whilst $R_3$, $R_4$ and A can have the meanings given under formula I but A is especially a radical of the partial formula Ia in which $Z_1$ represents hydrogen, or, preferably, is a radical of the partial formula Ib in which $Z_2$ represents lower alkyl, especially methyl, and $Z_3$ represents lower alkyl, especially methyl, or hydrogen, or is a radical of the partial formula Ic in which each of $R_5$ and $R_6$, independently of the other, represents hydrogen, lower alkyl, mono- or di-halogenated lower alkyl, or lower alkenyl or $R_5$ and $R_6$ together represent lower alkylene that is optionally interrupted by oxygen, sulphur or by optionally lower-alkylated nitrogen, and X represents $OR_7$ or $NR_8R_9$ in which $R_7$ represents hydrogen or lower alkyl and each of $R_8$ and $R_9$, independently of the other, represents hydrogen, lower alkyl, mono- or di-halogenated lower alkyl, or lower alkenyl or $R_8$ and $R_9$ together represent lower alkyene that is optionally interrupted by oxygen, sulphur or by optionally lower-alkylated nitrogen, or $R_6$ together with $R_7$ or $R_8$ represents lower alkylene having from 2 to 4 carbon atoms, and salts, especially pharmaceutically acceptable salts with bases, of such compounds in which $Z_1$, or $Z_3$ and optionally $Z_2$, or $R_7$ represent(s) hydrogen, for example the corresponding alkali metal salts, such as the sodium salts.

The invention relates more especially to compounds of the formula I in which $R_1$ represents allyl or 2-methallyl, and $R_2$ also represents one of these radicals or, preferably, methyl, $R_3$ represents hydrogen or, especially, methyl, and $R_4$ represents hydrogen, whilst A has the meaning given under formula I but has especially the preferred meanings indicated above, and in the radical of the formula Ib $Z_2$ is especially methyl and $Z_3$ is especially methyl or hydrogen, and in the radical of the formula Ic each of $R_5$ and $R_6$, independently of the other, represents hydrogen, methyl or 2-chloroethyl, and X represents $OR_7$ or $NR_8R_9$ in which each of $R_7$, $R_8$ and $R_9$ represents hydrogen or methyl, or $R_6$ together with $R_7$ represents ethylene which together with the atom group O-P-N forms a five-membered ring, or $R_6$ together with $R_8$ represents ethylene which together with the atom group N-P-N forms a five-membered ring, and salts, especially pharmaceutically acceptable salts, of such compounds in which $Z_1$, or $Z_3$ and optionally $Z_2$, or $R_7$ represent(s) hydrogen.

The invention relates also to the individual optical antipodes of compounds of the formula I and to mixtures of these optical antipodes, for example racemates or mixtures of diastereoisomers.

The invention relates most especially to the compounds and salts, preferably pharmaceutically acceptable salts, for example alkali metal salts, of corresponding salt-forming compounds, described in the Examples, and more especially 3-methyl-2-[[5-methyl-3-(2-methallyl)-4-oxo-5-thiazolidinylidene]-hyirazono-]4-oxo-5-thiazolidinyl hydrogen sulphate and methyl-3-methyl-2-[[5-methyl-3-(2-methallyl)-4-oxo-2-thiazolidinylidene]-hydrazono[-4-oxo-2-thiazolidinyl hydrogen phosphate, and especially their salts, such as pharmaceutically acceptable salts, such as, for example, the corresponding alkali metal salts, such as the sodium salts.

The novel compounds of the general formula I can be manufactured according to processes known per se. Thus they can be manufactured, for example, by (a) reacting a compound of the formula

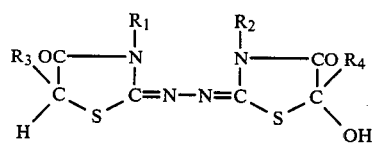

with a compound that introduces the radical of the partial formula Ia, Ib or Ic, or (b) for the manufacture of compounds of the formula I in which A is a radical of the formula Ia or Ib, in a compound of the formula

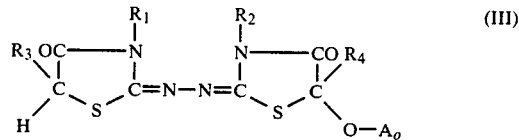

in which $A_o$ represents a radical of the formula

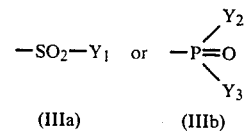

in which $Y_1$ or $Y_3$ represents a radical that can be replaced by the group $O-Z_1$ or $O-Z_3$, respectively, or by a salt form thereof, and $Y_2$ represents a radical $O-Z_2$ or a radical that can be replaced by the group $O-Z_2$ or by a salt form thereof, replacing the radical $Y_1$ or the radical $Y_3$ by the group $O-Z_1$ or $O-Z_3$, respectively, or by a salt form thereof, and optionally replacing the radical $Y_2$ by the group $O-Z_2$ or by a salt form thereof, or (c) for the manufacture of compounds of the formula I in which A is a radical of the formula Ic, in a compound of the formula

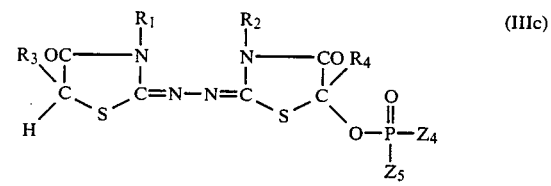

in which $Z_4$ represents a radical that can be replaced by the group $NR_5R_6$ or represents $NR_5R_6$, and $Z_5$ represents a radical that can be replaced by the group X or represents X, with the proviso that at least one of the groups $Z_4$ and $Z_5$ is other than the group $NR_5R_6$ or X, respectively, replacing the radical $Z_4$ by the group $NR_5R_6$ and/or replacing the radical $Z_5$ by the group X, and, if desired, converting a compound of the general formula I into a different compound of the general formula I, and/or, if desired, converting a salt obtainable according to the process into the free compound or into a different salt, and/or converting a compound of the formula I obtainable according to the process in which $Z_1$, or $Z_3$ and optionally $Z_2$, or $R_7$ represent(s) hydrogen into a salt thereof, and/or, if desired, separating an isomeric mixture obtainable according to the process into the isomers.

Compounds that introduce a radical of the formula Ia, Ib or Ic, are for example, sulphur trioxide, which may also be used in the form of complexes, such as the pyridine complex, or compounds of the general formulae

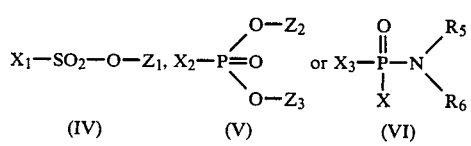

in which $X_1$, $X_2$ or $X_3$ represents reactive functionally modified hydroxy. The latter is, for example, especially hydroxy esterified by an inorganic or organic acid, such as hydroxy esterified by a hydrohalic acid or an aryl- or alkane-sulphonic acid, for example p-toluenesulphonic acid or methane- or ethane-sulphonic acid. $X_1$, $X_2$ or $X_3$ is especially halogen, such as bromine and, especially, chlorine. As starting materials of the formula IV there come into consideration, for example, chlorosulphonic acid and the lower alkyl esters thereof, as starting materials of the formula V, for example, di-lower alkyl- or lower alkylene-phosphorochloridates or alternatively corresponding phosphorobromidates, and as starting materials of the formula VI, for example, phosphoric acid halide di-lower alkylamine lower alkyl esters.

It is preferable to carry out the reaction with sulphur trioxide in an inert solvent or solvent mixture, the reaction with the sulphur trioxide/pyridine complex being carried out, for example, in methylene chloride or dimethylformamide or mixtures thereof with pyridine, and reactions with sulphur trioxide being carried out, for example, in dimethylformamide. The reaction temperatures are between approximately 0° and approximately 100° C.; the operation is preferably carried out at room temperature or at slightly elevated temperature. When using the sulphur trioxide pyridine complex there is obtained as a direct reaction product a pyridinium salt of compounds of the formula I which may be converted into the corresponding acids or, preferably, directly into other salts, such as, for example, alkali metal salts. When using sulphur trioxide, free acids are produced which, if desired, can be converted directly, that is to say without prior working up, into salts, for example alkali metal salts.

The reaction of compounds of the formula II with those of the formula IV, V or VI is preferable carried out in an inert, especially aprotic organic solvent, such as, for example, methylene chloride, acetonitrile, dimethylformamide or dimethyl sulphoxide, and preferably in the presence of an acid-binding agent, such as an organic base, for example tri-lower alkylamine, such as ethyldiisopropylamine or triethylamine, and also, for example, pyridine, or imidazole, or an alkali metal-lower alkoxido, for example sodium methoxide or ethoxide, or an inorganic base, for example sodium or potassium hydroxide, and in the presence of a basic ion exchanger. The reaction temperature selected is, for example, between 0° and approximately 100° C., preferably room temperature or slightly elevated temperature, and, if necessary, the reaction can be carried out in a closed vessel and/or under an inert gas atmosphere, such as a nitrogen atmosphere.

The starting materials of the formula II are known (for example German Offenlegungsschrift No. 2 405 395) or can be manufactured analogously to the compounds described therein.

In the starting materials of the formula III, radicals $Y_1$, or $Y_3$ and optionally $Y_2$, are, for example, esterified hydroxy groups, such as hydroxy groups esterified by strong acids, for example by mineral acids, and also by strong organic acids, or etherified hydroxy groups, for example hydroxy groups etherified by aliphatic, cycloaliphatic, aromatic or araliphatic radicals, such as corresponding optionally substituted hydrocarbon radicals. Esterified hydroxy groups are especially halogen, such as chlorine or bromine, whilst etherified hydroxy groups are, inter alia, aryloxy, such as phenoxy or p-nitrophenoxy, or aryl-lower alkoxy, such as, especially, benzyloxy, and also p-nitrobenzyloxy, and lower alkenyloxy, for example allyloxy, and also lower alkoxy, such as, for example, the groups $-OZ_1$, $-OZ_2$ and $-OZ_3$.

Compounds of the general formula I in which $Z_1$, or $Z_3$ and optionally $Z_2$, represent(s) hydrogen can be obtained by hydrolysis, such as by the action of water, optionally in the form of mixtures with suitable organic solvents, such as dioxan or lower alkanols, on compounds of the general formula III in which the radicals $Y_1$, or $Y_3$ and optionally $Y_2$, represent esterified hydroxy groups, such as halogen. Such compounds of the formula I can be produced from starting materials of the formula III in which $Y_1$, $Y_2$ and/or $Y_3$ represent suitably esterified hydroxy groups also in the absence of water, for example by transesterification, such as in the case of the action with a suitable alcohol, for example α-methylbenzyl alcohol. The same end products can be obtained, by basic hydrolysis, both from the afore-mentioned starting materials of the general formula III and from those in which $Y_1$, or $Y_3$ and optionally $Y_2$, represent aryloxy or aralkoxy groups, for example by the action of bases in the presence of at least equimolar amounts of water, preferably in water-containing organic solvents, such as corresponding lower alkanols or dioxan. As bases there may be used either organic, preferably tertiary, bases, such as those mentioned hereinbefore, or inorganic bases, such as sodium or potassium hydroxide, it being possible to obtain the reaction products either directly in the form of salts or, after treatment with an acidic reagent, in the form of free acids.

In starting materials of the formula III in which $Y_1$, and especially $Y_3$ and optionally $Y_2$, represent(s) etherified hydroxy, especially lower alkoxy and more especially methoxy, such a radical may advantageously be replaced by hydroxy by means of a nucleophilic substitution reaction; in this operation, in a corresponding starting material in which the two radicals $Y_2$ and $Y_3$ represent etherified hydroxy, for example methoxy, if desired only one of the etherified hydroxy groups can be cleaved. The cleaving can be effected by treatment of the corresponding starting material of the formula III with a suitable nucleophilic reagent, such a reagent preferably containing a hydroxy or, especially, mercapto group capable of being etherified or an amino group capable of being substituted, including quaternised. Such reagents are, inter alia, an optionally substituted thiophenolate compound, such as thiophenol in the presence of an inorganic or organic base, such as triethylamine, or a suitable urea, or, especially, thiourea compound, such as thiourea, and also a suitable, preferably sterically hindered, amine compound, such as a corresponding lower alkylamine, for example tert-butylamine, and also tri-lower alkylamine, such as trimethylamine, N-lower alkyl-morpholine or thiomorpholine, for example N-methylmorpholine, or pyridine.

The cleaving of an etherified hydroxy group $Y_1$, or $Y_3$ and optionally $Y_2$, can be effected also by treatment with a strong inorganic base, such as an alkali metal hydroxide, for example sodium or potassium hydroxide, preferably in the presence of an alcohol, such as a lower alkanol, for example ethanol, or ammonium hydroxide, or with a suitable neutral salt, especially an alkali metal or alkaline earth metal halide or thiocyanate, such as sodium iodide, barium iodide or sodium thiocyanate, this method being suitable especially for cleaving lower alkenyloxy groups, for example allyloxy groups, or aryl-lower alkoxy groups, for example benzyloxy groups Furthermore, suitably etherified hydroxy groups $Y_1$, or $Y_3$ and optionally $Y_2$, especially aromatically or araliphatically etherified hydroxy groups, such as optionally substituted phenoxy or benzyloxy, can be cleaved by hydrogenolysis, such as by treatment with hydrogen in the presence of a noble metal catalyst, such as a platinum or palladium catalyst, it being necessary to take care that a lower alkenyl group $R_1$ or $R_2$ is not also reduced.

Furthermore, in starting materials of the formula III, esterified hydroxy groups $Y_1$, or $Y_3$ and optionally $Y_2$, such as halogen, can be replaced by lower alkoxy by reacting a corresponding compound with a lower alkanol in the presence of a base under substantially anhydrous reaction conditions, or with a lower alkoxide of an alkali, alkaline earth or earth metal, such as a sodium or potassium methoxide, ethoxide or tert-butoxide.

The above reactions are carried out in a manner known per se in the absence or, preferably, in the presence of a suitable inert solvent, such as an optionally halogenated hydrocarbon, for example benzene or methylene chloride, a lower alkanol, for example methanol, dimethyl sulphoxide or acetonitrile, or a solvent mixture, and customarily under mild reaction conditions, preferably at temperatures of between approximately $-10°$ C. and approximately $100°$ C., especially at room temperature or slightly elevated temperatures up to approximately $50°$ C., if necessary in a closed vessel and/or under an inert gas atmosphere, such as a nitrogen atmosphere. The reaction products can be separated off in the form of free acids or can be converted directly into the salts, for example alkali metal salts.

Starting materials of the formula III in which $Y_1$, or $Y_3$ and optionally $Y_2$, represent(s) an etherified hydroxy group, such as lower alkoxy, aryloxy or aryl-lower alkoxy, can be manufactured in accordance with process (a).

It is also possible to obtain analogously to process (a) starting materials of the formula III in which $Y_1$, or $Y_3$ and optionally $Y_2$, represent(s) esterified hydroxy, especially halogen, such as chlorine, by reacting a compound of the formula II under mild reaction conditions, for example, with an equimolar amount of sulphuryl chloride or phosphorus oxychloride. The compounds of the formula III obtainable in this manner are preferably further reacted directly, in accordance with process (b), for example by treatment with water or a water-containing organic solvent, to form compounds of the formula I in which $Z_1$, or $Z_3$ and $Z_2$, represent(s) hydrogen, or salts thereof, or, for example, by treatment with alkali metal-lower alkoxides, such as sodium methoxide or ethoxide, to form compounds of the formula I in which $Z_1$, or $Z_3$ and optionally $Z_2$, represent(s) lower alkyl.

In compounds of the formula IIIc, a radical $Z_4$ that can be replaced by the group $NR_5R_6$ is hydroxy or reactive functionally modified hydroxy, and a radical $Z_5$ that can be replaced by the group X is reactive functionally modified hydroxy other than lower alkoxy. Such a functionally modified hydroxy group $Z_4$ or $Z_5$ has, for example, the meanings given above for $X_1$ and is especially halogen, such as bromine and, above all, chlorine.

Starting compounds of the formula IIIc are, for example, corresponding phosphoric acid triesters, phosphoric acid diesters, phosphoric acid monoesters, phosphoric acid chloride diesters, phosphoric acid amide chloride esters of phosphoric acid dichloride esters of the formula IIIc or corresponding bromides or dibromides. Such compounds of the formula IIIc are novel, with the exception of phosphoric acid triesters in which $Z_4$ and $Z_5$ represent lower alkoxy, phosphoric acid diesters in which $Z_4$ or $Z_5$ represents lower alkoxy, and phosphoric acid monoesters of the formula IIIc, and the invention relates also to these.

Conversion of $Z_5$ into hydroxy: For example, a compound of the formula IIIc in which $Z_4$ represents a group $NR_5R_6$ and $Z_5$ represents esterified hydroxy or etherified hydroxy other than lower alkoxy can be converted into a compound of the formula I in which X represents hydroxy by, for example, hydrolysing an esterified hydroxy group $Z_5$ such as halogen, to form a free hydroxy group by the action of water, optionally in the form of mixtures with suitable organic solvents, such as dioxan or lower alkanols. The same end products can be obtained by basic hydrolysis both from the above-mentioned compounds of the formula IIIc and from compounds of the formula IIIc containing aryloxy or aralkoxy groups as $Z_5$, for example by the action of at least equimolar amounts of water in the presence of bases, preferably in water-containing organic solvents, such as corresponding lower alkanols or dioxan. There can be used as bases in this operation either organic, preferably tertiary, bases, such as those mentioned under process (a), or inorganic bases, such as alkali metal carbonates or hydroxides, for example sodium or potassium carbonates or hydroxides; an excess should be avoided. The reaction products can be obtained either directly in the form of salts or, after treatment with an acidic reagent, in the form of free acids.

Compounds of the formula I in which X represents $OR_7$ and $R_7$ represents hydrogen can be obtained also by treating a compound of the formula IIIc, in which $Z_5$ represents a hydroxy group that is etherified as indicated above and is other than lower alkoxy, with a strong inorganic base, such as an alkali metal hydroxide, for example sodium or potassium hydroxide, preferably in the presence of an alcohol, such as a lower alkanol, for example ethanol, or ammonium hydroxide, or with a suitable neutral salt, especially an alkali metal or an alkaline earth metal halide or thiocyanate, such as sodium iodide, barium iodide or sodium thiocyanate, this method being suitable especially for cleaving lower alkenyloxy, for example allyloxy, groups, or aryl-lower alkoxy, for example benzyloxy, groups.

In addition, suitably etherified hydroxy groups $Z_5$, especially araliphatically etherified hydroxy groups, such as optionally substituted benzyloxy, can be cleaved by means of hydrogenolysis, such as by treatment with hydrogen in the presence of a noble metal catalyst, such as a platinum or palladium catalyst; in this operation care must be taken that a lower alkenyl group $R_1$ or $R_2$ is not also reduced.

Conversion of $Z_5$ into lower alkoxy or $NR_8R_9$: It is also possible to convert compounds of the formula IIIc in which $Z_5$ represents an esterified hydroxy group into compounds of the formula I in which X represents $OR_7$ and $R_7$ represents lower alkyl or in which X represents the group $NR_8R_9$ by reacting a corresponding compound of the formula IIIc in which $Z_5$ represents, for example, halogen, for example, with a lower alkanol or a compound of the formula $HNR_8R_9$ (VII) in the presence of a base under substantially anhydrous reaction conditions or with a lower alkoxide of an alkali metal or an alkaline earth metal, such as sodium or potassium methoxide, ethoxide or tert.-butoxide.

Conversion of $Z_4$ into $NR_5R_6$: It is also possible to treat compounds of the formula IIIc in which $Z_5$ represents X and Z represents reactive functionally modified hydroxy, for example correspondingly esterified hydroxy, such as halogen, for example chlorine, with a compound of the formula $HNR_5R_6$ (VIII), for example according to the process described above, and to convert them into compounds of the formula I. A starting material of the formula IIIc in which $Z_4$ represents hydroxy can be converted into a compound of the formula I, for example, by reaction with a suitable reagent, such as with N,N'-dicyclohexyl carbodiimide or carbonyl diimidazole, and then with an amine of the formula VIII.

Conversion of $Z_4$ and $Z_5$ into $NR_5R_6$ and X: Starting compounds of the formula IIIc in which $Z_4$ and $Z_5$ represent reactive functionally modified hydroxy as described above or $Z_5$ represents such a radical that is other than lower alkoxy and $Z_4$ represents hydroxy can be converted directly into compounds of the formula I. Such starting compounds of the formula IIIc can be, for example, phosphoric acid dichloride esters or dibromide esters of the formula IIIc. For example, they can be reacted with a compound of the formula VII or VIII, and compounds of the formula I can be obtained in which X and $NR_5R_6$ have the same meaning.

Such starting compounds of the formula IIIc of this type can also be reacted with a compound of the formula $$Y\text{—Alk—}NHR_5 \qquad IX$$

in which Y represents hydroxy or an amino group substituted by $R_9$ and Alk represents alkylene which separates Y from the nitrogen atom by from 2 to 4 carbon atoms, to form compounds of the formula I in which $R_6$ together with X and the atom grouping P-N forms a five- to seven-membered ring. Starting compounds of the formula IX are known or can be manufactured in known manner.

The reaction of compounds of the formula IIIc to form compounds of the formula I is preferaby carried out in an inert, especially aprotic, organic solvent, such as, for example, methylene chloride, acetonitrile, dimethylformamide or dimethyl sulphoxide, and, if $Z_4$ and/or $Z_5$ represent(s) esterified hydroxy, preferably in the presence of an acid-binding agent, such as an organic base, for example a tri-lower alkylamine, such as ethyldiisopropylamine or triethylamine, also, for example, pyridine or imidazole, or an alkali metal lower alkoxide, for example sodium methoxide or ethoxide, or an inorganic base, for example sodium or potassium hydroxide, or a basic ion exchanger. There is selected as reaction temperature, for example, a temperature of from 0° to approximately 100° C., preferably room temperature or a slightly elevated or reduced temperature, and, if necessary, the reaction can be carried out in a closed vessel and/or in an inert gas atmosphere, such as a nitrogen atmosphere.

Starting materials of the formula IIIc can be manufactured, for example, by reacting a compound of the formula II with a compound of the formula

in which $X_4$ has the meaning given under formula VI. Accordingly, there come into consideration as starting materials of the formula X, for example, halogenated and/or esterified phosphoric acids or phosphoric acid amides, such as phosphoric acid chloride esters, phosphoric acid chloride diesters, phosphoric acid amide dichlorides or alternatively corresponding bromides or dibromides.

Starting materials of the formula X are known or can be manufactured analogously to known processes.

The reaction of compounds of the formula II with compounds of the formula X can be carried out, for example, in the same manner as the reaction of compounds of the formula II with compounds of the formula VI.

It is also possible to convert a compound of the formula IIIc firstly into a different compound of the formula IIIc and only then to convert the latter into a compound of the formula I. Thus, for example, a phosphoric acid lower alkyl ester thiazolidinyl ester of the formula IIIc can be converted into a phosphoric acid chloride lower alkyl ester thiazolidinyl ester of the formula IIIc by reaction with acid chlorides of sulphur- or phosphorus-containing acids, such as, for example, thionyl chloride or phosphorus pentachloride, in an inert solvent, such as a chlorinated hydrocarbon, for example chloroform.

Alternatively, it is also possible, for example, to carry out a reaction in which a phosphoric acid dilower alkyl ester thiazolidinyl ester of the formula IIIc is converted into a phosphoric acid thiazolidinyl ester of the formula IIIc by replacing the two lower alkoxy groups by hydroxy groups, for example by reaction with halosilanes of the formula $HalSi(R)_3$ and subsequent hydrolysis of the silyl esters formed as primary products.

In the formula $HalSi(R)_3$, Hal represents chlorine, bromine or iodine and $(R)_3$ represents a combination of three radicals, which may be the same or different and each of which is lower alkyl, such as tert.-butyl, ethyl or methyl, or substituted or unsubstituted aryl, such as phenyl. Suitable silanes are, for example, chlorotrimethylsilane, chlorotriethylsilane, tert.-butylchlorodimethylsilane, chloromethyldiphenylsilane or the corresponding bromine or iodine compounds. Especially the corresponding iodine compounds, but also the bromine compounds, can be manufactured in situ by, for example, reacting one of the chlorine compounds mentioned with an alkali metal or alkaline earth metal iodide (bromide), such as lithium iodide (bromide), sodium iodide (bromide) or magnesium bromide. Suitable solvents for these reactions are aprotic solvents, such as, for example, acetonitrile, methylene chloride or carbon tetrachloride.

Compounds of the formula I obtainable according to the invention can be converted into different compounds of the formula I in a manner known per se. Thus, in accordance with the above process modification (b), compounds of the formula I in which A has the partial formula Ia or, especially, Ib, and $Z_1$ or $Z_2$ represents lower alkyl and $Z_3$ represents hydrogen or lower alkyl, a lower alkyl group $Z_1$ or $Z_2$ representing especially methyl, can be converted into compounds of the formula I in which the radical A has the partial formula Ia or Ib in which $Z_1$ or $Z_2$ represents hydrogen and $Z_3$ represents hydrogen or lower alkyl. Analogously, in compounds of the formula I in which A has the partial formula Ic and X represents lower alkoxy, the lower alkoxy group X can be converted into a hydroxy group X.

A further possibility of converting compounds of the formula I in which X represents lower alkoxy and, especially, methoxy, or $Z_1$ or $Z_2$ represent lower alkyl, into compounds of the formula I in which X represents hydroxy, or $Z_1$ or $Z_2$ represent hydrogen is offered by reaction with halosilanes of the formula $HalSi(R)_3$ and subsequent hydrolysis of the silyl esters formed as primary products. Both halosilanes of the formula $HalSi(R)_3$ and their use are described above.

Furthermore, free acids of the formula I ($Z_1$ or $Z_2$ represent hydrogen or X represents hydroxy) can be obtained from the above-mentioned esters of the formula I by de-alkylating a lower alkyl ester of the formula I (X represents lower alkoxy or $Z_1$ or $Z_2$ represent lower alkyl) under phase-transfer conditions. There come into consideration as reagents for this purpose alkali metal halides, such as sodium chloride or sodium bromide, and/or quaternary ammonium salts, such as, for example, benzyltriethylammonium chloride or bromide. The halogen anion must be used in equimolar amounts but the amounts of ammonium salt can be limited to catalytic amounts if an alkali metal halide supplies halogen anions. Suitable solvents are aprotic polar solvents, such as acetone, acetonitrile or dimethylformamide, or aprotic non-polar solvents, such as benzene or toluene. The operation is preferably carried out at elevated temperature, for example from 30° to 100° C.

It is also possible to convert compounds of the formula I in which A has the partial formula Ic and X represents hydroxy into compounds of the formula I in which X represents an amino group $NR_8R_9$ by, for example, bringing the hydroxy group into a reactive form, for example by reaction with carbonyl diimidazole or dicyclohexyl carbodiimide, and converting the intermediate product into a phosphoric acid diamide ester of the formula I by treatment with an amine of the formula $HNR_8R_9$ (VII).

It is also possible in compounds of the formula I in which A has the partial formula Ic and X represents $OR_7$ and $R_7$ represents hydrogen to replace the hydrogen by lower alkyl, for example by treatment of the particular compound with a reactive ester of a lower alkanol and a strong acid, such as a corresponding lower alkyl halide, for example a lower alkyl chloride, bromide or iodide, or a corresponding arene- or lower alkane-sulphonic acid lower alkyl ester, for example p-toluenesulphonic acid lower alkyl ester or methanesulphonic acid lower alkyl ester.

Compounds of the formula I in which $R_6$ together with $R_7$ or $R_8$, or $Z_2$ with $Z_3$ forms a lower alkylene group can also be obtained from other compounds of the formula I. For example, a compound of the formula I in which $R_6$ and $R_8$ each represents hydrogen or in which $R_6$ and $R_7$ each represents hydrogen or in which $Z_2$ and $Z_3$ each represents hydrogen can be reacted with a compound of the formula $$\text{Hal-Alk-Hal}' \quad \text{XI}$$

in which each of Hal and Hal', independently of the other, represents halogen, such as, for example, chlorine, bromine or iodine, to form a compound of the formula I in which $R_6$ together with $R_7$ or $R_8$, or in which $Z_2$ together with $Z_3$ forms a lower alkylene group.

Starting compounds of the formula XI are known or can be manufactured in known manner.

The above reactions are carried out in a manner known per se either in the absence, but preferably in the presence, of a suitable inert solvent, such as an optionally halogenated hydrocarbon, for example benzene or methylene chloride, a lower alkanol, for example methanol, dimethyl sulphoxide or acetonitrile, or a mixture of solvents, and customarily under mild reaction conditions, preferably at temperatures of from approximately $-10°$ to approximately 100° C., especially at room temperature or at a slightly elevated temperature of up to approximately 50° C., if necessary in a closed vessel and/or in an inert gas atmosphere, for example a nitrogen atmosphere. The reaction products can be separated off in the form of free acids or can be converted directly into salts, for example alkali metal salts.

Salts of salt-forming compounds of the formula I obtainable according to the invention can be converted into the free compounds in a manner known per se, for example by treatment with an acidic reagent, such as an acid, or into different salts by salt interchange.

Salts of compounds of the formula I that are suitable for salt formation, especially pharmaceutically acceptable salts, such as, for example, those mentioned above, can be manufactured in a manner known per se, for example by treatment with a suitable base, such as an alkali metal hydroxide, ammonia or a salt-forming amine.

Mixtures of isomers can be separated into the pure isomers in a manner known per se, racemic mixtures inter alia by means of physical separation, for example fractional crystallisation or distillation, or chromatography, inter alia high pressure liquid chromatography, and racemates inter alia with the formation of salts with optically active bases and separation of the resulting salt mixtures, for example by fractional crystallisation.

The invention relates also to those embodiments of the process in which a starting material is formed under the reaction conditions, or in which a reactant is optionally in the form of its salts.

The starting materials used for carrying out the reactions according to the invention are advantageously those which result in the groups of end products given special mention at the beginning and especially in the end products specifically described or pointed out.

The present invention relates also to the use of the novel compounds as pharmacologically active, especially as carcinostatically active, compounds. The daily doses of such compounds are, for mammals, depending upon species, age, individual condition, and on the method of administration, between approximately 2 mg and approximately 250 mg, especially between approximately 5 mg and approximately 100 mg, per kg body weight, and within this range the doses in the case of parenteral administration, for example intramuscular or subcutaneous injection, or intravenous infusion, are generally lower than in the case of enteral, that is to say oral or rectal, administration. The compounds of the formula I and pharmaceutically acceptable salts of such compounds having salt-forming properties are used orally or rectally preferably in dosage unit forms, such as tablets, dragées or capsules or suppositories, and parenterally especially in the form of injectable solutions, emulsions or suspensions or in the form of infusion solutions, there coming into consideration as solutions especially solutions of salts.

The invention relates also to pharmaceutical preparations for enteral, for example oral or rectal, or parenteral administration, which contain a therapeutically effective amount of a compound of the formula I or a pharmaceutically acceptable salt of such a compound having salt-forming properties, optionally together with a pharmaceutically acceptable carrier or carrier mixture, it being possible for these carriers to be inorganic or organic, and solid or liquid. Corresponding dosage unit forms, especially for oral use, for example dragées, tablets or capsules, preferably contain from approximately 50 mg to approximately 500 mg, especially from approximately 100 mg to approximately 400 mg, of a compound of the formula I or a pharmaceutically acceptable salt of a corresponding compound that is capable of salt formation together with pharmaceutically acceptable carriers.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, maize, wheat, rice or potato starch, gelatine, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores can be provided with suitable coatings that are optionally resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Further pharmaceutical preparations for oral administration are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain substances which increase the viscosity, for example sodium carboxymethylcellulose, sorbitol and/or dextran, and, optionally, stabilisers.

The pharmaceutical preparations of the present invention can be manufactured in a manner known per se. for example by means of conventional mixing, granulating, confectioning, dissolving and lyophilising processes. Thus pharmaceutical preparations for oral use can be obtained by mixing the active ingredient with solid carriers, optionally granulating a resulting mixture and, if desired or necessary after the addition of suitable adjuncts, processing the mixture or granulate to form tablets or dragée cores.

The following Examples illustrate the invention described above but do not restrict the scope of the invention in any way. Temperatures are given in degrees Centigrade.

EXAMPLE 1

56 g (0.35 mol) of sulphur trioxide/pyridine complex are added to a solution of 32.8 g (0.1 mol) of 5-hydroxy-3-methyl-2-[[5-methyl-3-(2-methallyl)-4-oxo-2-thiazolidinylidene]-hydrazono]-4-thiazolidinone in 700 ml of methylene chloride and 200 ml of anhydrous pyridine and the mixture is stirred at 20°–25° for 20 hours. Then 700 ml of water are added and the mixture is stirred for a further 20 minutes and the two layers are separated. The methylene chloride solution is dried over magnesium sulphate and concentrated by evaporation in a water-jet vacuum. 500 ml of diethyl ether are added to the residue and the yellow reaction product that precipitates out is filtered with suction and washed three times with acetone and then with diethyl ether. The resulting pyridinium [3-methyl-2-[[5-methyl-3-(2-methallyl)-4-oxo-5-thiazolidinylidene]-hydrazono]-4-oxo-5-thiazolidinyl]-sulphate melts at 187°.

For conversion into the sodium salt, 48.7 g (0.10 mol) of the above pyridinium salt are dissolved in 1100 ml of methylene chloride and 100 ml of methanol and, while stirring well, a sodium methoxide solution, prepared from 2.3 g (0.10 mol) of sodium and 50 ml of methanol, is added dropwise thereto and the desired sodium salt precipitates out. After the addition of 300 ml of ether the salt is filtered with suction and washed twice with methylene chloride, once with diethyl ether/methanol 4:1 and then with ether. After drying in a high vacuum at 60°, the resulting sodium [3-methyl-2-[[5-methyl-3-(2-methallyl)-4-oxo-2-thiazolidinylidene]-hydroazono-4-oxo-5-thiazolidinyl]-sulphate melts at 195° (with decomposition).

EXAMPLE 2

In a manner analogous to that described in Example 1, using as starting materials 31.4 g (0.10 mol) of 5-hydroxy-2-[(3-methyl-4-oxo-2-thiazolidinylidene)-hydrazono]-3-(2-methallyl)-4-thiazolidinone and 56 g (0.35 mol) of sulphur trioxide pyridine complex there is obtained pyridinium [2-[(3-methyl-4-oxo-2-thiazolidinylidene)-hydrazono]-3-(2-methallyl)-4-oxo-5-thiazolidinyl]-sulphate having a melting point of 161°–161°; and also in a manner analogous to that described in Example 1, the corresponding sodium salt, having a melting point of 216° (with decomposition), is obtained from 47.4 g (0.10 mol) of the pyridinium salt in 800 ml of methylene chloride and a sodium methoxide solution of 2.3 g (0.10 mol) of sodium and 200 ml of methanol.

EXAMPLE 3

To a solution of 31.4 g (0.1 mol) of 5-hydroxy-2-[(3-methyl-4-oxo-2-thiazolidinylidene)-hydrazono]-3-(2-methallyl)-4-thiazolidinone in 500 ml of methylene chloride and 100 ml of pyridine there is added a suspension that has been prepared beforehand from a solution of 23.3 g (0.34 mol) of chlorosulphonic acid in 400 ml of methylene chloride by the dropwise addition of 180 ml of pyridine at a reaction temperature of from −10° to 0° under a nitrogen atmosphere. The resulting reaction mixture is stirred at 20°–25° for 20 hours. Then 700 ml of water are added and the mixture is stirred for a further 20 minutes and the two layers are separated. The methylene chloride solution is dried over magnesium sulphate and then concentrated by evaporation in a water-jet vacuum. The resulting pyridinium [2-[(3-methyl-4-oxo-2-thiazolidinylidene)-hydrazono]-3-(2-methallyl)-4-oxo-5-thiazolidinyl]-sulphate melts at 190°–191°.

For conversion into the sodium salt, 47.3 g (0.10 mol) of the above pyridinium salt are dissolved in 600 ml of methylene chloride and 400 ml of dimethylformamide and, while stirring well, a 2.95% strength sodium methoxide solution in methanol is added dropwise thereto. The sodium salt is precipitated out by the addition of 1500 ml of diethyl ether; the salt is filtered with suction, washed once with a 4:1 mixture of diethyl ether and methanol and then with diethyl ether. After drying under a high vacuum at 60°, the sodium 2-[(3-methyl-4-oxo-2-thiazolidinylidene)-hydrazono]-3-(2-methallyl)-4-oxo-5-thiazolidinyl]-sulphate melts at 216° (with decomposition).

EXAMPLE 4

In a manner analogous to that described in Example 3, using as starting materials 60.1 g (0.20 mol) of 3-allyl-5-hydroxy-2-[(3-methyl-4-oxo-2-thiazolidinylidene)-hydrazono]-4-thiazolidinone, 46.6 ml (0.70 mol) of chlorosulphonic acid and 250 ml of pyridine in 700 ml of methylene chloride and, for conversion into the sodium salt, 100 ml of a 3.4% strength sodium methoxide solution in methanol, there is obtained sodium [3-allyl-2-[(3-methyl-4-oxo-2-thiazolidinylidene)-hydrazono]-4-oxo-5-thiazolidinyl]-sulphate having a melting point of 217° (decomposition).

EXAMPLE 5

In a manner analogous to that described in Example 1, using as starting materials 68 g (0.20 mol) of 3-allyl-2-[(3-allyl-5-methyl-4-oxo-2-thiazolidinylidene)-hydrazono]-5-hydroxy-4-thiazolidinone, 81.6 g (0.7 mol) of chlorosulphonic acid, 300 ml of pyridine in 400 ml of methylene chloride and, for conversion into the sodium salt, 50 ml of a 7.6% strength sodium methoxide solution in methanol, there is obtained sodium [3-allyl-2-[(3-allyl-5-methyl-4-oxo-2-thiazolidinylidene)-hydrazono]-4-oxo-5-thiazolidinyl]-sulphate having a melting point of 190° (decomposition).

EXAMPLE 6

While stirring, 21 ml (0.2 mol) of dimethyl phosphorochloridate are added dropwise to a solution of 33 g (0.10 mol) of 5-hydroxy-3-methyl-2-[[5-methyl-3-(2methallyl)-4-oxo-2-thiazolidinylidene]-hyirazono]-4-thiazolidinone and 43 ml of ethyldiisopropylamine in 250 ml of methylene chloride. The reaction is at first slightly exothermic and the reaction temperature is maintained at 25° by cooling. After the addition is complete, the reaction mixture is stirred at room temperature for a further 2 hours. The mixture is then extracted by shaking firstly with 100 ml of ice-cold 2N hydrochloric acid and then with two 100 ml portions of water. The methylene chloride solution is dried over magnesium sulphate and concentrated by evaporation in a water-jet vacuum. Dimethyl-[3-methyl-2-[[5-methyl-3-(2-methallyl)-4-oxo-2-thiazolidinylidene]-hydrazono]4-oxo-5-thiazolidinyl]-phosphate remains behind as the residue and, after recrystallising once from diethyl ether, melts at 99°–103°.

EXAMPLE 7

While stirring, 56 ml of triethylamine are added dropwise to a solution of 22 g (0.05 mol) of dimethyl-[3-methyl-2-[[5-methyl-3-(2-methallyl)-4-oxo-2-thiazolidinylidene]-hydrazono]-4-oxo-5-thiazolidinyl]-phosphate and 26 ml of thiophenol in 70 ml of dioxan, the reaction temperature rising to 40°. The reaction mixture is then stirred at room temperature for a further two hours. Then 400 ml of diethyl ether are added and a heavy oil separates out.

The ether solution is decanted off and the oil that remains is dissolved in 200 ml of isopropanol and, while stirring, a sodium methoxide solution, prepared from 1.15 g (0.05 mol) of sodium and 30 ml of methanol, is added thereto. Sodium methyl-[3-methyl-2-[[5-methyl-3-(2-methallyl)-4-oxo-2-thiazolidinylidene]-hydrazono]-4-oxo-5-thiazolidinyl]-phosphate separates out. This is filtered with suction, washed with a small quantity of isopropanol and diethyl ether and then dried in a high vacuum at 60° for 15 hours. Melting point 146°–150°.

This product is a diastereoisomeric mixture which can be separated into the two racemates, for example by means of high pressure liquid chromatography using a stationary phase of silica gel with a chemically bonded C 18 phase (for example Hibar LiChroCart HPLC cartridge, filled with LiChrosorb RP 18, column composition: 250×4 mm, by Merck AG, Darmstadt, Federal Republic of Germany) and a liquid phase, for example a 40:40:20 mixture of methanol/water/0.01 molar aqueous sodium dihydrogenphosphate.

EXAMPLE 8

While stirring at 5°–10°, 16.7 ml (0.12 mol) of triethylamine are added dropwise to a suspension of 30 g (0.10 mol) of 2-[(3-allyl-4-oxo-2-thiazolidinylidene)-hydrazono]-5-hydroxy-3-methyl-4-thiazolidinone and 21.7 g (0.15 mol) of dimethyl phosphorochloridate in 250 ml of methylene chloride. The reaction is slightly exothermic and the suspended substances, with the exception of the triethylamine hydrochloride that is formed, enter into solution. When the addition is complete, the reaction mixture is stirred at room temperature for a further one hour. The mixture is then extracted by shaking firstly with 200 ml of ice-cold water and then with 100 ml of ice-cold saturated sodium bicarbonate solution. The methylene chloride solution is dried over magnesium sulphate and concentrated under reduced pressure until crystallisation begins. 100 ml of diethyl ether are added to the residue and the [2-[(3-allyl-4-oxo-2-thiazolidinylidene)-hydrazono]-3-methyl-4-oxo-5-thiazolidinyl]-dimethyl phosphate is filtered with suction. Melting point 147°–148°.

The starting material may be prepared as follows: (a) While stirring, 17.1 g (0.10 mol) of 3-allyl-2,4-thiazolidinedione-2-hydrazone [colourless oil, cf. U.S. Pat. No. 3,699,116, Example 8 (a) to (d)] and 8.0 g (0.11 mol) of methyl isothiocyanate are boiled under reflux in 70 ml of isopropanol for 2 hours, and 3-allyl-2,4-thiazolidinedione-2-(4-methyl-3-thiosemicarbazone) separates out in the form of a coarse crystalline precipitate. This is cooled with ice, filtered with suction and washed with a 1:1 mixture of pentane and diethyl ether. Melting point: 148°–151°. (b) 11.0 g (0.12 mol) of glyoxylic acid monohydrate are dissolved in 40 ml of dioxan and the solution is then diluted with 200 ml of carbon tetrachloride. Then, while stirring, 24.4 g (0.10 mol) of 3-allyl-2,4-thiazolidinedione-2-(4-methyl-3-thiosemicarbazone) are introduced. The mixture is then heated and, with the simultaneous dropwise addition of 120 ml of carbon tetrachloride, 120 ml of an azeotropic mixture of carbon tetrachloride and water are distilled off in a descending condenser. The mixture is cooled to 20°, and the crystal mass is diluted with 100 ml of diethyl ether; the crystals are filtered with suction and then washed with diethyl ether. The resulting 2-[(3-allyl-4-oxo-2-thiazolidinylidene)-hydrazono]-5-hydroxy-3-methyl-4-thiazolidinone melts at 209°–210°.

EXAMPLE 9

In a manner analogous to that described in Example 8, using as starting materials 31.4 g (0.10 mol) of 2-[(3-allyl-5-methyl-4-oxo-2-thiazolidinylidene)-hydrazono]-5-hydroxy-3-methyl-4-thiazolidinone, 21.7 g (0.15 mol) of dimethyl phosphorochloridate and 16.7 ml (0.12 mol) of triethylamine in 250 ml of methylene chloride there is obtained [2-(3-allyl-5-methyl-4-oxo-2-thiazolidinylidene)-hydrazono]-3-methyl-4-oxo-5-thiazolidinyl]-dimethyl phosphate having a melting point of 102°–107°.

The starting material is prepared as follows: (a) 11.0 g (0.12 mol) of glyoxylic acid monohydrate are dissolved in 40 ml of dioxan and the solution is then diluted with 200 ml of carbon tetrachloride. Then, while stirring, 25.8 g (0.10 mol) of 3-allyl-5-methyl-2,4-thiazolidinedione-2-(4-methyl-3-thiosemicarbazone) [cf. U.S. Pat. No. 3,699,116, Example 8(a) to (e)] are introduced. The reaction mixture is then heated and, with the simultaneous dropwise addition of 120 ml of carbon tetrachloride, 120 ml of an azeotropic mixture of carbon tetrachloride and water are distilled off in a descending condenser. The mixture is cooled to 20° and the crystal mass is diluted with 100 ml of diethyl ether and 200 ml of pentane; the crystals are filtered with suction and washed with a 2:1 mixture of pentane and diethyl ether. The resulting 2-[(3-allyl-5-methyl-4-oxo-2-thiazolidinylidene)-hydrazono]-5-hydroxy-3-methyl-4-thiazolidinone melts at 164°–166°.

EXAMPLE 10

While stirring, 41.4 ml (0.30 mol) of triethylamine are added dropwise to a suspension of 40.8 g (0.10 mol) of 2-[(3-allyl-4-oxo-2-thiazolidinylidene)-hydrazono]-3-methyl-4-oxo-5-thiazolidinyl]-dimethyl phosphate and 20.5 ml (0.20 mol) of thiophenol in 250 ml of isopropanol and the reaction temperature rises to 30°. The clear yellow reaction solution is then stirred at 35° for a further 4 hours. Then, at 30°–35°, a sodium methoxide solution prepared from 2.3 g (0.10 mol) of sodium and 50 ml of methanol is added dropwise thereto. Sodium [2-[(3-allyl-4-oxo-2-thiazolidinylidene)-hydrazono]-3-methyl-4-oxo-5-thiazolidinyl]-methyl phosphate separates out. This is filtered with suction and washed with isopropanol and diethyl ether. After recrystallisation from a 4:1 mixture of isopropanol and water, the product melts at 200°–205° (with decomposition).

EXAMPLE 11

In a manner analogous to that described in Example 10, using as starting materials 42.2 g (0.10 mol) of [2-[(3-allyl-5-methyl-4-oxo-2-thiazolidinylidene-hydrazono]-3-methyl-4-oxo-5-thiazolidinyl]-dimethyl phosphate, 20.5 ml (0.20 mol) of thiophenol and 41.4 ml (0.30 mol) of triethylamine in 250 ml of isopropanol and, for conversion into the sodium salt, treating the product with 23 ml of a 10% strength (w/v) methanolic sodium methoxide solution, there is obtained sodium [2-[(3-allyl-5-methyl-4-oxo-2-thiazolidinylidene)-hydrazono]-3-methyl-4-oxo-5-thiazolidinyl]-methyl phosphate having a melting point of 190° (decomposition).

EXAMPLE 12

While stirring and cooling at 4°, a solution of 0.4 g of tert.-butylamine in 5 ml of methylene chloride is added dropwise over a period of 7 minutes to a mixture of 2.18 g of dimethyl-[3-methyl-2-[[5-methyl-3-(2-methallyl)-4-oxo-2-thiazolidinylidene]-hydrazono]-4-oxo-5-thiazolidinyl]-phosphate and 12 ml of methylene chloride under a nitrogen atmosphere. The temperature of the clear yellow solution is allowed to rise to room temperature; the solution is stirred for 3½ hours and 1 ml of tert.-butylamine is added. Stirring is carried out for a further 16 hours at room temperature, a further 2 ml of tert.-butylamine are then added to the reaction mixture and stirring is continued for a further 29½ hours. The mixture is diluted with 20 ml of diethyl ether and the precipitate is filtered off and washed with a 1:3 mixture of methylene chloride and diethyl ether and then with diethyl ether, yielding (N-methyl-tert.-butylammonium) methyl-[3-methyl-2-[[5-methyl-3-(2-methallyl)-4-oxo-2-thiazolidinylidene]-hydrazono]-4-oxo-5-thiazolidinyl]-phosphate which melts at 216°–217° (with decomposition) and which is dried at room temperature under a high vacuum for 15 hours. It can be converted into the sodium salt, for example by treatment with a methanolic sodium methoxide solution.

EXAMPLE 13

While stirring, a mixture of 2.2 g of dimethyl-[3-methyl-2-[[5-methyl-3-(2-methallyl)-4-oxo-2-thiazolidinylidene]-hydrazono]-4-oxo-5-thiazolidinyl]-phosphate and 0.38 g of thiourea in 2.5 ml of methanol are boiled under reflux at a bath temperature of 70°–80° for 6 hours and a solution is produced which is left to stand for 16 hours and which then solidifies to form a crystal mass. This is diluted with 4 to 5 ml of diethyl ether, and the solid material is crushed, filtered off and washed with a 2:1 mixture of diethyl ether and methanol and then with diethyl ether. The resulting (S-methylisothiuronium) methyl-[2-methyl-2-[[5-methyl-3-(2-methallyl)-4-oxo-2-thiazolidinylidene]-hydrazono]-4- oxo-5-thiazolidinyl]-phosphate melts at 189°–191° (with decomposition) and can be converted into the sodium salt, for example by treatment with a methanolic sodium methoxide solution.

EXAMPLE 14

While stirring, 120 ml of 1N hydrochloric acid are added to a solution of 49.4 g of sodium methyl-[3-methyl-2-[[5-methyl-3-(2-methallyl)-4-oxo-2-thiadiazolidinylidene]-hydrazono]-4-oxo-5-thiazolidinyl]-phosphate in 800 ml of water (deionised). A thick semigelatinous mass is produced which is dissolved in 1500 ml of dioxan at 30°–35°. The solution is diluted with 2500 ml of methylene chloride; the mixture is shaken and the layers are allowed to separate. The aqueous phase is separated off and extracted twice using 200 ml of methylene chloride each time. The combined organic solutions are washed once with 400 ml of a 1:1 mixture of a concentrated aqueous sodium chloride solution and with water and dried over 200 g of magnesium sulphate for 5 minutes. The mixture is filtered, washed with a 1:2 mixture of dioxan and methylene chloride and the filtrate is concentrated by evaporation under reduced pressure at a bath temperature of 45°–50° to a volume of 800 ml and a crystalline precipitate is formed which is filtered off and washed twice with a small quantity of dioxan and then with diethyl ether. There is thus obtained methyl-[3-methyl-2-[[5-methyl-3-(2-methallyl)-4-oxo-2-thiazolidinylidene]-hydrazono]-4-oxo-5-thiazolidinyl]-hydrogen phosphate which melts at 193°–194°.

EXAMPLE 15

While stirring, a suspension of 7 g of methyl-[3-methyl-2-[[5-methyl-3-(2-methallyl)-4-oxo-2-thiazolidinylidene]-hydrazono]-4-oxo-5-thiazolidinyl]-hydrogen phosphate (Example 14) in 40 ml of distilled water is adjusted to pH 7 by the addition of approximately 4% strength aqueous potassium hydroxide and the slightly turbid solution is treated with approximately 0.5 g of activated carbon and filtered. The filtrate is concentrated under reduced pressure to a weight of approximately 15 g and the syrup-like residue, which contains some solid substance, is dissolved in 50 ml of isopropanol and, while stirring, diethyl ether is added in portions. A viscous precipitate is produced; a relatively large amount of diethyl ether is added and the supernatant solution is decanted off; approximately 40 ml of acetone are added to the residue, producing a powder-like precipitate. Diethyl ether is again added but the precipitate is not filtered and is drained into another vessel with the aid of acetone; 20 ml of isopropanol are added and the whole is diluted with 150 ml of diethyl ether, yielding potassium methyl-[3-methyl-2-[[5-methyl-3-(2-methallyl)-4-oxo-2-thiazolidinylidene]-hydrazono] -4-oxo-5-thiazolidinyl]-phosphate, which can now be filtered, and which is dried under reduced pressure at 60° for 24 hours. Melting point 167°–170° (decomposition from 177°).

EXAMPLE 16

While stirring, a suspension of 8 g of methyl-(3-methyl-2-[[5-methyl-3-(2-methallyl)-4-oxo-2-thiazolidinylidene]-hydrazono]-4-oxo-5-thiazolidinyl]-hydrogen phosphate (Example 14) in 50 ml of distilled water is adjusted to pH 7-8 with an approximately 4% strength aqueous ammonium hydroxide solution. The slightly turbid solution is cleared with activated carbon and filtered and the filtrate is concentrated under reduced pressure to a weight of 20 g. This is diluted with 80 ml of isopropanol, and diethyl ether is added until the mixture begins to become turbid. Crystallisation can be initiated by inoculation. The ammonium methyl-[3-methyl-2-[[5-methyl-3-(2-methallyl)-4-oxo-2-thiazolidinylidene]-hydrazono]-4-oxo-5-thiazolidinyl]-phosphate is filtered off and dried in a high vacuum at room temperature for 20 hours. Melting point: 195°–197°.

EXAMPLE 17

While stirring, a 5% aqueous solution of 2-hydroxyethylamine is added, in portions, to a suspension of 1 g of methyl-[3-methyl-2-[[5-methyl-2-(2-methallyl)-4-oxo-2-thiazolidinylidene]-hydrazono]-4-oxo-5-thiazolidinyl]-hydrogen phosphate (Example 14) in 10 ml of distilled water until a pH value of 7-8 has been reached. The solution is cleared with 0.3 g of activated carbon, filtered and concentrated under reduced pressure to a weight of approximately 2 g. The semi-solid residue is taken up in 7 ml of absolute ethanol, and diethyl ether is added until the mixture begins to become turbid. The precipitate so obtained is dissolved in approximately 20 ml of methanol, a small quantity of activated carbon is added to the solution and the whole is filtered; the now clear filtrate is concentrated to a volume of approximately 5 ml. The (2-hydroxyethylammonium) methyl-[3-methyl-2-[[5-methyl-3-(2-methallyl)-4-oxo-2-thiazolidinylidene]-hydrazono]-4-oxo-5-thiazolidinyl]-phosphate is caused to crystallise by the addition of diethyl ether and then filtered off. Melting point: 186°–187°.

EXAMPLE 18

A suspension of 1 g of methyl-[3-methyl-2-[[5-methyl-3-(2-methallyl)-4-oxo-2-thiazolidinylidene]-hydrazono]-4-oxo-5-thiazolidinyl]-hydrogen phosphate (Example 14) in 10 ml of distilled water is adjusted to pH 7-8 by the addition in portions, while stirring, of a 5% aqueous solution of tri-(2-hydroxyethyl)-amine. A clear solution is obtained which becomes turbid after about 5 minutes and is concentrated under reduced pressure to a weight of 3 g. The mixture is diluted with 20 ml of absolute ethanol, stirred with 0.5 g of activated carbon and filtered. The now clear filtrate is concentrated under reduced pressure to a weight of approximately 3 g, the [tri-(2-hydroxyethyl)-ammonium] methyl-[3-methyl-2-[[5-methyl-3-(2-methallyl)-4-oxo-2-thiazolidinylidene]-hydrazono]-4-oxo-5-thiazolidinyl]-phosphate beginning to crystallise. 10 ml of absolute ethanol and, in portions, 10 ml of diethyl ether are added, the salt is filtered off and dried under a high vacuum at 40° for 6 hours. Melting point: 145°–146°.

EXAMPLE 19

While stirring, 23.6 g (0.15 mol) of phosphoric acid chloride dimethylamide methyl ester are added dropwise to a solution of 33 g (0.10 mol) of 5-hydroxy-3-methyl-2-[[5-methyl-3-(2-methylallyl)-4-oxo-2-thiazolidinylidene] -hydrazono]-4-thiazolidinone and 43 ml of ethyldiisopropylamine in 250 ml of methylene chloride. The whole is left to react for 24 hours at 25° and then 100 ml of water at 0° are added. Vigorous stirring is carried out for 5 minutes and the organic phase is separated off, washed with water and, after being dried over magnesium sulphate, is concentrated under a water-jet vacuum. Phosphoric acid dimethylamide methyl ester-[3-methyl-2-[[5-methyl-3-(2-methylallyl)-4-oxo-2-thiazolidinylidene]-hydrazono]-4-oxo-5-thiazolidinyl]-ester remains as residue. M.p. 126°–128°, IR (CH$_2$Cl$_2$): 1735 (s), 1610 (s), 1375 (m), 1320 (m), 1045 (m), 995 (s) cm$^{-1}$ and others.

EXAMPLE 20

45 g (0.10 mol) of phosphoric acid dimethylamide methyl ester-[3-methyl-2-[[5-methyl-3-(2-methylallyl)-4-oxo-2-thiazolidinylidene]-hydrazono]-4-oxo-5-thiazolidinyl]-ester are dissolved in 100 ml of dioxan under pure nitrogen and, while stirring, 22 g (0.30 mol) of tert.-butylamine are added. Stirring is carried out for a total of 15 hours at 50°; the product begins to separate after approximately 12 hours. 100 ml of diethyl ether are then added and the precipitated tert.-butylammonium salt of phosphoric acid dimethylamide-[3-methyl-2-[[5-methyl-3-(2-methylallyl)-4-oxo-2-thiazolidinylidene]-hydrazono]-4-oxo-5-thiazolidinyl]-ester is filtered off with suction and then washed with a small amount of diethyl ether.

M.p. 184° (decomposition), IR (KBr): 1730 (s), 1605 (s), 1375 (m), 1315 (m), 1220 (s), 1060 (s), 1015 (m), 990 (m) cm$^{-1}$ and others.

EXAMPLE 21

50.8 g (0.10 mol) of the tert.-butylammonium salt of phosphoric acid dimethylamide-[3-methyl-2-[[5-methyl-3-(2-methylallyl)-4-oxo-2-thiazolidinylidene]-hydrazono]-4-oxo-5-thiazolidinyl]-ester are dissolved in 250 ml of glacial acetic acid and, over a period of 15 minutes, while stirring, a solution of 9.90 g (0.103 mol) of methanesulphonic acid in 20 ml of glacial acetic acid is added; the product begins to precipitate. Stirring is carried out for 30 minutes at room temperature and phosphoric acid dimethylamide-[3-methyl-2-[[5-methyl-3-(2-methylallyl)-4-oxo-2-thiazolidinylidene]-hydrazono]-4-oxo-5-thiazolidinyl]-ester is filtered off with suction and then washed with 50 ml of glacial acetic acid and 150 ml of diethyl ether.

EXAMPLE 22

4.4 g (0.01 mol) of phosphoric acid dimethylamide-[3-methyl-2-[[5-methyl-3-(2-methylallyl)-4-oxo-2-thiazolidinylidene]-hydrazono]-4-oxo-5-thiazolidinyl]-ester are dissolved in 50 ml of methanol and, while stirring, a sodium methoxide solution prepared from 0.23 g (0.01 mol) of sodium and 5 ml of methanol is added. Diethyl ether is added and the sodium salt of phosphoric acid dimethylamide-[3-methyl-2-[[5-methyl-3-(2-methylallyl)-4-oxo-2-thiazolidinylidene]-hydrazono]-4-oxo-5-thiazolidinyl]-ester separates out. The latter is filtered off with suction, washed with a small amount of diethyl ether and then dried for 15 hours at 50° under a high vacuum.

IR (KBr): 1730 (s), 1615 (s), 1430 (m), 1385 (s), 1325 (m), 1240 (s), 1075 (s), 1020 (m), 990 (m), 925 (m), 840 (m), 750 (m), 735 (m) cm$^{-1}$.

EXAMPLE 23

2.2 g (0.02 mol) of thiophenol are added to a suspension of 4.5 g (0.01 mol) of phosphoric acid dimethylamide methyl ester-[3-methyl-2-[[5-methyl-3-(2-methylallyl)-4-oxo-2-thiazolidinylidene]-hydrazono]-4-oxo-5-thiazolidinyl]-ester in 25 ml of 2-propanol. While stirring, 3.04 ml (0.03 mol) of triethylamine are added dropwise thereto, the reaction temperature rising to 30°. The solution is heated at 40° until it becomes clear and then left to cool to room temperature; the reaction mixture is maintained at this temperature for 24 hours. The mixture is then cooled to 5° and 4 ml of a 2.5N methanolic sodium methoxide solution are added dropwise thereto, whereupon a gelatinous precipitate forms. The whole is diluted with 25 ml of ether and filtered with suction. The sodium salt of phosphoric acid dimethylamide-[3-methyl-2-[[5-methyl-3-2-methylallyl)-4-oxo-2-thiazolidinylidene]-hydrazono]-4-oxo-5-thiazolidinyl]-ester so obtained is recrystallised from methanol/2-propanol.

M.p. 201° (decomposition). IR (KBr): 1730 (s), 1615 (s), 1430 (m), 1385 (s), 1325 (m), 1240 (s), 1075 (s), 1020 (m), 990 (m), 925 (m), 840 (m), 750 (m), 735 (m) cm$^{-1}$.

EXAMPLE 24

While stirring and under a nitrogen atmosphere, 4.7 g (0.03 mol) of 2-chloro-3-methyl-1,3,2-oxazaphospholidine-2-oxide [manufactured according to A. Takamizawa et al., Chem. Pharm. Bull., 25, 2900 (1977)] are added to 6.6 g (0.02 mol) of 5-hydroxy-3-methyl-2-[[5-methyl-3-(2-methylallyl)-4-oxo-2-thiazolidinylidene]-hydrazono]-4-thiazolidinone in 30 ml of methylene chloride. Over a period of 15 minutes, a solution of 3.35 ml (2.43 g; 0.024 mol) of triethylamine in 10 ml of methylene chloride is added dropwise at 3° to this mixture. Stirring is carried out for 90 minutes over an ice-bath and for 1 hour at room temperature. 100 ml of diethyl ether are then added and the whole is extracted by shaking twice with 100 ml of water each time in a separating funnel. The organic phase is dried over magnesium sulphate and then concentrated by evaporation under a water-jet vacuum. 3-methyl-2-[3-methyl-2-[[5-methyl-3-(2-methylallyl)-4-oxo-2-thiazolidinylidene]-hydrazono]-4-oxo-5-thiazolidinoxy]-2-oxo-1,3,2-oxazaphospholidine remains as residue which, for purification, is recrystallised from methylene chloride/isopropanol.

M.p. 158°–160°. IR (CH$_2$Cl$_2$): 1740, 1615, 1380, 1045, 1005, 940, 845 cm$^{-1}$.

EXAMPLE 25

In a manner analogous to that described in Example 24 starting from 7.5 g (0.025 mol) of 3-allyl-5-hydroxy-2-[[3-methyl-4-oxo-2-thiazolidinylidene]-hydrazono]-4-thiazolidinone, 7.8 g (0.05 mol) of 2-chloro-3-methyl-1,3,2-oxazaphospholidine-2-oxide and 4.53 ml (0.0325 mol) of triethylamine in 50 ml of methylene chloride there is obtained 2-[3-allyl-2-[[3-methyl-4-oxo-2-thiazolidinylidene]-hydrazono]-4-oxo-5-thiazol-idinoxy]-3-methyl-2-oxo-1,3,2-oxazaphospholidine having a melting point of 184°–185°.

IR (CH$_2$Cl$_2$): 1740, 1650, 1380, 1040, 1005, 940, 845 cm$^{-1}$.

EXAMPLE 26

In a manner analogous to that described in the preceding Examples, the following compounds according to the invention can be manufactured:

phosphoric acid di-(2-chloroethyl)-amide-[3-methyl-2-[[5-methyl-3-(2-methylallyl)-4-oxo-2-thiazolidinylidene]-hydrazono]-4-oxo-5-thiazolidinyl]-ester and its salts, phosphoric acid di-(2-chloroethyl)-amide methyl ester-[3-methyl-2-[[5-methyl-3-(2-methylallyl)-4-oxo-2-thiazolidinylidene]-hydrazono]-4-oxo-5-thiazolidinyl]-ester, IR: 1740, 1615, 1380, 1040, 1000 cm$^{-1}$, phosphoric acid bis-dimethylamide-[3-methyl-2-[[5-methyl-3-(2-methylallyl)-4-oxo-2-thiazolidinylidene]-hydrazono]-4-oxo-5-thiazolidinyl]-ester, IR: 1740, 1610, 1375, 1045, 1005 cm$^{-1}$, phosphoric acid di-(2-chloroethyl)-amide-dimethylamide-[3-methyl-2-[[5-methyl-3-(2-methylallyl)-4-oxo-2-thiazolidinylidene]-hydrazono]-4-oxo-5-thiazolidinyl]-ester, IR: 1740, 1615, 1380, 1040, 1005 cm$^{-1}$, 2-[3-(methyl-2-[[5-methyl-3-(2-methylallyl)-4-oxo-2-thiazolidinylidene]-hydrazono]-4-oxo-5-thiazolidinoxy]-2-oxo-1,3,2-oxazaphospholidine, IR: 1740, 1615, 1380, 1040, 1005, 940, 845 cm$^{-1}$, 2-[3-methyl-2-[[5-methyl-3-(2-methylallyl)-4-oxo-2-thiazolidinylidene]-hydrazono]-4-oxo-5-thiazolidinoxy]-2-oxo-1,3,2-diazaphospholidine, IR: 1740, 1615, 1375, 1040, 1000 cm$^{-1}$, 1,3-dimethyl-2-[3-methyl-2-[[5-methyl-3-(2-methylallyl)-4-oxo-2-thiazolidinylidene]-hydrazono]-4-oxo-5-thiazol-idinoxy]-2-oxo-1,3,2-diazaphospholidine, IR: 1740, 1615, 1380, 1040, 1005 cm$^{-1}$.

EXAMPLE 27

Coated tablets containing 300 mg of sodium [3-methyl-2-[[5-methyl-3-(2-methallyl)-4-oxo-2-thiazolidinylidene]-hydrazono]-4-oxo-5-thiazolidinyl]-sulphate can be manufactured as follows:

Composition for 10,000 tablets sodium [3-methyl-2-[[5-methyl-3-(2-methallyl) -4-oxo-2-thiazolidinylidene]-hydrazono-4-oxo-5-thiazolidinyl]sulphate: 3000.0 g
maize starch: 630.0 g
colloidal silica: 200.0 g
magnesium stearate: 20.0 g
stearic acid: 50.0 g
sodium carboxymethyl starch: 250.0 g
water: q.s.

A mixture of the sodium [3-methyl-2-[[5-methyl-3-(2-methallyl)-4-oxo-2-thiazolidinylidene]-hydrazono]-4-oxo-5-thiazolidinyl]-sulphate, 50 g of maize starch and the colloidal silica is worked into a moist mass with a starch paste of 250 g of maize starch and 2.2 kg of demineralised water. This is forced through a sieve of 3 mm mesh width and dried at 45° in a fluidised bed drier for 30 minutes. The dry granulate is pressed through a sieve of 1 mm mesh width, mixed with a previously sieved mixture (1 mm sieve) of 330 g of maize starch, the magnesium stearate, the stearic acid and the sodium carboxymethyl starch and pressed into slightly curved tablets.

The tablet compacts are coated in a confectioning boiler of 45 cm diameter by uniform spraying for 30 minutes with a solution of 20 g of shellac and 40 g of hydroxypropylmethylcellulose (low viscosity) in 110 g of methanol and 1350 g of methylene chloride; drying is carried out by simultaneously blowing in air at 60°.

Instead of the above-mentioned active ingredient it is also possible to use the same amount of a different active ingredient from the preceding Examples, such as sodium [3-allyl-2-[(3-methyl-4-oxo-2-thiazolidinylidene)-hydrazono]-4-oxo-5-thiazolidinyl]-sulphate, dimethyl-[3-methyl-2-[[5-methyl-3-(2-methallyl)-4-oxo-2-thiazolidinylidene]-hydrazono]-4-oxo-5-thiazolidinyl]-phosphate, sodium methyl-[3-methyl-2-[[5-methyl-3-(2-methallyl)-4-oxo-2-thiazolidinylidene]-hydrazono]-4-oxo-5-thiazolidinyl]-phosphate, or (2-hydroxyethylammonium) methyl-[3-methyl-2-[[5-methyl-3-(2-methallyl)-4-oxo-2-thiazolidinylidene]-hydrazono]-4-oxo-5-thiazolidinyl]-phosphate.

EXAMPLE 28

Hard gelatine capsules are filled with, in each case, 300 mg of sodium 3-methyl-2-[[5-methyl-3-(2-methallyl)-4-oxo-2-thiazolidinylidene]-hydrazono]-4-oxo-5-thiazolidinyl]-sulphate, mixed with 60 mg of rice starch.

Instead of the above active ingredient it is also possible to use the same quantity of sodium or (2-hydroxymethylammonium) methyl-[3-methyl-2-[[5-methyl-3-(2-methallyl)-4-oxo-2-thiazolidinylidene]-hydrazono]-4-oxo-5-thiazolidinyl]-phosphate.

EXAMPLE 29

Ampoules are filled with, in each case, 5 ml of a sterile 4% strength aqueous solution of sodium [3-methyl-2-[[5-methyl-3-(2-methallyl)-4-oxo-2-thiazolidinylidene]-hydrazono]-4-oxo-5-thiazolidinyl]-sulphate corresponding to 200 mg of active ingredient, and the ampoules are sealed and examined.

Instead of the above active ingredient it is also possible to use the same quantity of sodium or (2-hydroxyethylammonium) methyl-[3-methyl-2-[[5-methyl-3-(2-methallyl)-4-oxo-2-thiazolidinylidene]-hydrazono]-4-oxo-5-thiazolidinyl]-phosphate.

I claim:

1. Compounds of the formula

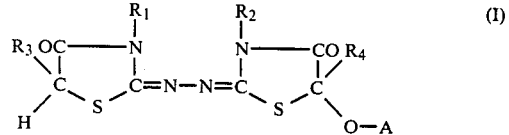

in which one of the symbols $R_1$ and $R_2$ represents an alkyl radical having 3 or 4 carbon atoms that is unsaturated in the 2,3-position and the other represents such a radical or lower alkyl, each of $R_3$ and $R_4$, independently of the other, represents hydrogen or methyl, and A represents a radical of the formula

in which each of $R_5$ and $R_6$, independently of the other, represents hydrogen, lower alkyl, halogenated lower alkyl, or lower alkenyl or $R_5$ and $R_6$ together represent lower alkylene that is optionally interrupted by oxygen, sulphur or by optionally substituted nitrogen, and X represents $OR_7$ or $NR_8R_9$ in which $R_7$ represents hydrogen or lower alkyl and each of $R_8$ and $R_9$, independently of the other, represents hydrogen, lower alkyl, halogenated lower alkyl, or lower alkenyl or $R_8$ and $R_9$ together represent lower alkylene that is optionally interrupted by oxygen, sulphur or by optionally substituted nitrogen, or $R_6$ together with $R_7$ or $R_8$ represents a lower alkylene group, salts of compounds of the general formula I in which $R_7$ represents hydrogen, the individual isomers of compounds of the formula I and mixtures of these isomers.

2. Compounds as claimed in claim 1, in which one of the symbols $R_1$ and $R_2$ represents allyl, 1-methallyl, 2-methallyl or 2-propynyl, and the other also represents one of these groups or methyl, and $R_3$, $R_4$ and A have the meanings given in claim 1, and salts of such compounds of the formula I in which $R_7$ represents hydrogen.

3. Compounds as claimed in claim 1, in which one of the radicals $R_1$ and $R_2$ represents allyl or 2-methallyl, and the other also represents one of these groups or methyl, and $R_3$, $R_4$ and A have the meanings given in claim 1, and salts of such compounds of the formula I in which $R_7$ represents hydrogen.

4. Compounds as claimed in claim 1, in which one of the radicals $R_1$ and $R_2$ represents allyl or 2-methallyl, and the other also represents one of these groups or methyl, $R_3$ and $R_4$ have the meanings given in claim 1, and A represents a radical of the partial formula Ic in which each of $R_5$ and $R_6$, independently of the other, represents hydrogen, lower alkyl, mono- or di-halogenated lower alkyl, or lower alkenyl or $R_5$ and $R_6$ together represent lower alkylene that is optionally interrupted by oxygen, sulphur or by optionally lower-alkylated nitrogen, and X represents $OR_7$ or $NR_8R_9$ in which $R_7$ represents hydrogen or lower alkyl and each of $R_8$ and $R_9$, independently of the other, represents hydrogen, lower alkyl, mono- or di-halogenated lower alkyl, or lower alkenyl or $R_8$ and $R_9$ together represent lower alkyene that is optionally interrupted by oxygen, sulphur or by optionally lower-alkylated nitrogen, or $R_6$ together with $R_7$ or $R_8$ represents lower alkylene having from 2 to 4 carbon atoms, and salts of such compounds of the formula I in which $R_7$ represents hydrogen.

5. Compounds as claimed in claim 1, in which $R_1$ represents allyl or 2-methallyl and $R_2$ also represents one of these radicals or methyl, $R_3$ represents hydrogen or methyl, $R_4$ represents hydrogen, and A represents a radical of the partial formula Ic, in which each of $R_5$ and $R_6$, independently of the other, represents hydrogen, methyl or 2-chloroethyl, and X represents $OR_7$ or $NR_8R_9$ in which each of $R_7$, $R_8$ and $R_9$ represents hydrogen or methyl, or $R_6$ together with $R_7$ represents ethylene which together with the atom group O-P-N forms a five-membered ring, or $R_6$ together with $R_8$ represents ethylene which together with the atom group N-P-N forms a five-membered ring, and salts of such compounds of the formula I in which $R_7$ represents hydrogen.

6. Phosphoric acid dimethylamide methyl ester-[3-methyl-2-[[5-methyl-3-(2-methylallyl)-4-oxo-2-thiazolidinylidene]-hydrazono]-4-oxo-5-thiazolidinyl]-ester according to claim 1.

7. Phosphoric acid dimethylamide-[3-methyl-2-[[5-methyl-3-(2-methylallyl)-4-oxo-2-thiazolidinylidene]hydrazono]-4-oxo-5-thiazolidinyl]-ester and salts thereof according to claim 1.

8. 3-methyl-2-[3-methyl-2-[[5-methyl-3-(2-methylallyl)-4-oxo-2-thiazolidinylidene]-hydrazono]-4-oxo-5-thiazolidinoxy]-2-oxo-1,3,2-oxazaphospholidine according to claim 1.

9. 2-[3-allyl-2-[[3-methyl-4-oxo-2-thiazolidinylidene]-hydrazono]-4-oxo-5-thiazolidinoxy]-3-methyl-2-oxo-1,3,2-oxazaphospholidine according to claim 1.

10. A pharmaceutical composition for treating neoplastic diseases containing a therapeutically effective amount of a compound of the formula I or of a salt thereof according to claim 1, together with a pharmaceutically acceptable carrier.

11. A method of treatment of neoplastic diseases in a mammal, comprising the administration of a therapeutically effective amount of a compound of the formula I or of a salt thereof according to claim 1 to said mammal.

* * * * *